United States Patent
Fisher et al.

(10) Patent No.: US 8,381,780 B2
(45) Date of Patent: Feb. 26, 2013

(54) LIFT AND SUPPORT ASSEMBLIES AND METHODS FOR COLLAPSIBLE BAG CONTAINERS OF VESSELS AND BIOREACTORS

(75) Inventors: Michael Fisher, Ashland, MA (US); Parrish M. Galliher, Littleton, MA (US)

(73) Assignee: Xcellerex, Inc., Marlborough, MA (US)

(*) Notice: Subject to any disclaimer, the term of this patent is extended or adjusted under 35 U.S.C. 154(b) by 506 days.

(21) Appl. No.: 12/469,469

(22) Filed: May 20, 2009

(65) Prior Publication Data

US 2009/0290962 A1 Nov. 26, 2009

Related U.S. Application Data

(60) Provisional application No. 61/055,408, filed on May 22, 2008.

(51) Int. Cl.
*B65B 3/04* (2006.01)

(52) U.S. Cl. ....... 141/314; 141/114; 294/68.3; 414/287; 414/808

(58) Field of Classification Search .................. 414/287, 414/808; 141/114, 314; 294/68.3
See application file for complete search history.

(56) References Cited

U.S. PATENT DOCUMENTS

| | | | | |
|---|---|---|---|---|
| 1,755,854 A | * | 4/1930 | Weed | 294/68.3 |
| 1,852,061 A | * | 4/1932 | Peyser et al. | 292/246 |
| 4,541,765 A | * | 9/1985 | Moore | 414/267 |
| 4,883,201 A | * | 11/1989 | Poulton | 222/105 |
| 5,067,504 A | * | 11/1991 | Coleman, III | 134/172 |
| 5,529,177 A | * | 6/1996 | Podd et al. | 206/204 |
| 6,019,432 A | * | 2/2000 | Bonerb | 298/24 |
| 2004/0261889 A1 | * | 12/2004 | Elgan et al. | 141/10 |
| 2005/0272146 A1 | | 12/2005 | Hodge et al. | |
| 2008/0068920 A1 | | 3/2008 | Galliher | |

FOREIGN PATENT DOCUMENTS

| | | |
|---|---|---|
| EP | 1 078 886 A2 | 2/2001 |
| EP | 2 020 433 A2 | 2/2009 |
| WO | WO 02/074141 A1 | 9/2002 |
| WO | WO 2004/071959 A2 | 8/2004 |
| WO | WO 2008/088379 A2 | 7/2008 |
| WO | WO 2008/089510 A1 | 7/2008 |

OTHER PUBLICATIONS

Definition of circumference from "thefreedictionary.com/p/circumference".*
Ring defintion, http://dictionary.reference.com/browse/ring.*
Rectangular ring.*
Rectangular.*
European Patent Office—Search Report dated May 6, 2011 (6 Pages) English, Application No. 09006881.8-2401 / 2123745.

* cited by examiner

*Primary Examiner* — Scott Lowe (57) ABSTRACT

Disclosed are a lift assembly and methods that may be used to raise a component of a system, a component such as a collapsible bag to be used as a reactor for performing chemical or biological reactions, and/or to position the collapsible bag for use. Use of the lift assembly may allow for the automated assembly of the systems described herein. In some cases, trauma to the system components is minimized.

17 Claims, 5 Drawing Sheets

LIFT AND SUPPORT ASSEMBLIES AND METHODS FOR COLLAPSIBLE BAG CONTAINERS OF VESSELS AND BIOREACTORS

RELATED APPLICATIONS

This application claims priority under 35 U.S.C. §119(e) to U.S. Provisional Patent Application No. 61/055,408, filed May 22, 2008, and entitled "Lift and Support Assemblies and Methods for Collapsible Bag Containers of Vessels and Bioreactors," the teachings of which are incorporated herein by reference in their entireties.

FIELD OF INVENTION

The disclosed invention relates generally to systems for containing and manipulating fluids in collapsible bag containers, and to mechanisms and methods for supporting and/or lifting collapsible bag containers or portions thereof within a reusable support structure or vessel containing and/or supporting the collapsible bag.

BACKGROUND

Biological materials including, for example, mammalian, fungal, yeast, marine organisms, tissue or organs, plant or insect cells and microbial cultures can be processed using bioreactors. Traditional bioreactors, typically designed as either stationary pressurized vessels or as disposable bioreactors utilizing plastic, sterile bags, may be used. Improvements to such systems would be beneficial.

SUMMARY OF THE INVENTION

Disclosed herein is a lift assembly for lifting or supporting an article within a vessel configured to contain a volume of fluid, the lift assembly comprising: an assembly support structure adapted to be attached to a top portion of the vessel; a lifting component mounted on the assembly support structure and vertically movable relative to the assembly support structure, the lifting component adapted to be attached to the article to be supported or lifted; and a motive device for vertically moving the lifting component relative to the assembly support structure.

Another embodiment of the invention is a system comprising: a vessel comprising a collapsible bag configured to contain a volume of a fluid, the vessel comprising a support structure surrounding and containing the collapsible bag; and a lift assembly attached to a top portion of the vessel, the lift assembly comprising an assembly support structure and a lifting component vertically movable relative to the assembly support structure, and wherein the lifting component is configured and arranged to lift at least an upper portion of the collapsible bag to convert the collapsible bag from a collapsed to an uncollapsed configuration and to support the collapsible bag in the uncollapsed configuration.

In another aspect, the invention relates to a method for lifting an article contained within a vessel, comprising: extending a lifting component from a top portion to a bottom portion of a vessel, the vessel having an interior portion configured to contain a volume of fluid, and an entry port positioned at the bottom portion of the vessel; directing the lifting component towards the entry port positioned at the bottom portion of the vessel such that at least a part of the lifting component is positioned at or near the entry port; attaching an article to at least a portion of the lifting component; and raising the lifting component and the article towards the top portion of the vessel.

The disclosed invention provides a number of advantages. For example, use of the lift assembly may allow for the automated assembly of the systems described herein, eliminating the need for the operator to lift one or more components of the system during installation or removal. In some cases, trauma to the system components is minimized. In addition, the systems and methods described herein may enable consistently repeatable installation of system components.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

Disclosed herein are systems and methods for supporting and/or lifting single use containers such as collapsible bag containers, or portions thereof, within a reusable support structure or vessel containing and/or supporting the collapsible bag. In some embodiments, a lift assembly is provided. The lift assembly may be used to raise a component of the system, for example, a collapsible bag, and/or position and/or support it for use. Methods for raising and/or positioning an article with the lift assembly may comprise, for example, hoisting the article or portion thereof within the interior of a vessel and/or from a region exterior of the vessel to the interior of the vessel.

Use of a disclosed lift assembly in certain embodiments may allow for the automated assembly of certain systems described herein, thereby eliminating or reducing the need for an operator to lift one or more components of the system during installation or removal. In some cases, trauma to the system components may be minimized. In addition, the systems and methods described herein may enable consistently repeatable installation of system components.

The following documents are incorporated herein by reference in their entirety: U.S. patent application Ser. No. 12/124,039, filed May 20, 2008, entitled "Continuous Perfusion Bioreactor System," by Galliher et al; U.S. patent application Ser. No. 11/879,033, filed Jul. 13, 2007, entitled "Environmental Containment Systems," by G. Hodge, et al.; International Patent Application Serial No. PCT/US2007/014050 filed on Jun. 15, 2007 and entitled, "Gas Delivery Configurations, Foam Control Systems, and Bag Molding Methods and Articles for Collapsible Bag Vessels" by Fisher et al.; U.S. patent application Ser. No. 11/147,124, filed Jun. 6, 2005, entitled "Disposable Bioreactor Systems and Methods," by G. Hodge, et al., published as U.S. Patent Application Publication No. 2005/0272146 on Dec. 8, 2005; and international Patent Application No. PCT/US2005/002985, filed Feb. 3, 2005, entitled "System and Method for Manufacturing," by G. Hodge, et al., published as WO 2005/076093 on Aug. 18, 2005.

Although much of the description herein involves an exemplary application of the present invention related to bioreactors (and/or biochemical and chemical reaction systems), the invention and its uses are not so limited, and it should be understood that aspects of the invention can also be used in other settings, including, for example, mixing systems and those involving containment or processing systems in general. As the terms are used herein, bioreactor, reactor system, biochemical reaction systems, and chemical reaction systems have the same meaning and are used interchangeably and synonymously to mean a reactor system used to perform at least part of a biological, chemical, or pharmaceutical process.

It should also be understood that while many examples provided herein involve the use of collapsible bags or flexible containers, aspects of the invention can be integrated with systems involving non-collapsible bags, rigid containers, and other configurations involving liquid containment.

In one embodiment of the invention, a lift assembly is provided. The lift assembly may be part of a system which includes a vessel configured to contain a volume of liquid. A vessel "configured to contain a volume of fluid," as the expression is used herein, indicates that the vessel may be fluid-tight and that the fluid may contact directly the interior surface of the vessel, or that the vessel may not have interior surfaces in direct contact with the fluid, but instead may contain and support a liner or container, such as a collapsible bag, contained with the vessel, and which contains the fluid. The vessel may be a part of a reactor system. In some embodiments, the disclosed lift assembly may be used to raise an article such as a collapsible bag within the vessel and/or to position such article for use.

Figure 1:
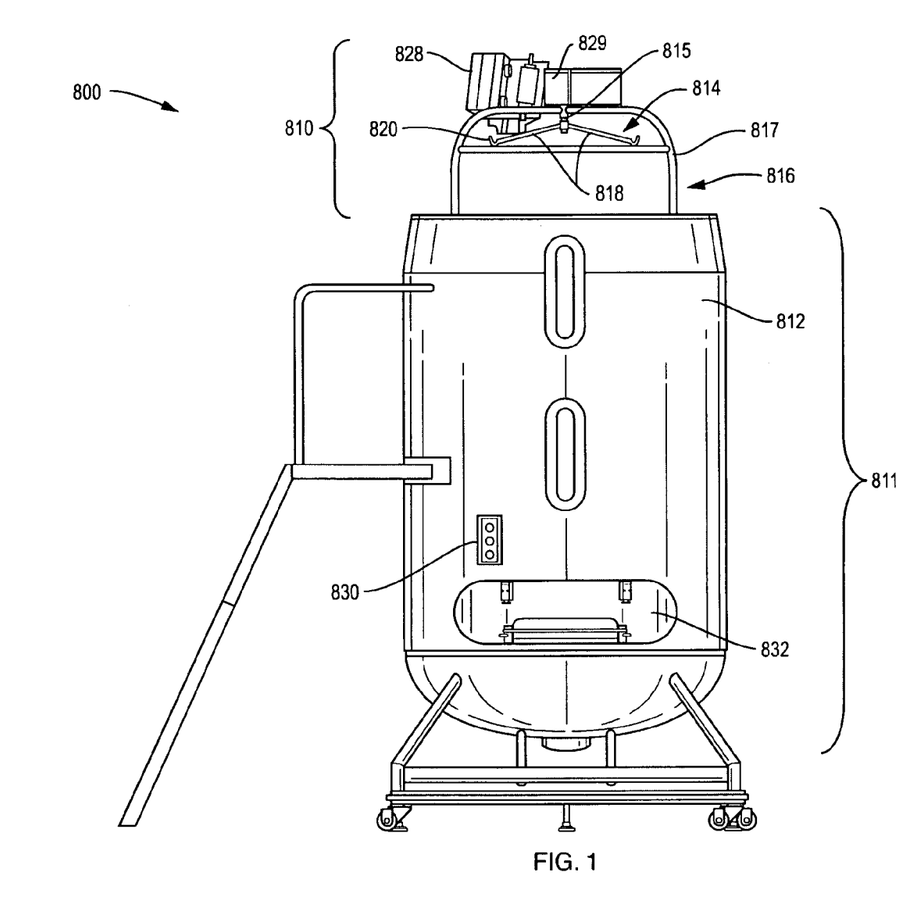
FIG. 1 is a schematic representation of a bioreactor system comprising a lift assembly according to one embodiment of the invention.

FIG. 1 depicts an exemplary system 800 including a lift assembly 810. The disclosed lift assembly 810 provides a method for moving, positioning and/or supporting an article, such as a collapsible bag container, in a vessel 811. Non-limiting examples of articles that may be manipulated using the lift assembly 810 include collapsible bags, impellers, spargers, or any other component of system 800. In some embodiments, vessel 811 comprises a containment structure 812, that may comprise any suitable unit capable of supporting an interior container. The containment structure 812 may be, for example, a stainless steel tank. In other embodiments of the invention, support structures may comprise any suitable material, for example, polymers, glass, or other metals, in any suitable configuration, for example, enclosed containers or support scaffolds.

As shown in FIG. 1, the lift assembly 810 may be attached to a top portion of a vessel 811 via an assembly support structure 816. The assembly support structure 816 may comprise one or more bars, plates, or any other structural component suitable for supporting the desired mechanical load to be lifted by the lift assembly 810. The assembly support structure 816 may be permanently attached, for example by welding, to the vessel 811 or it may be removably attached, for example by bolts, screws, or clamps. Suitable materials for construction of the assembly support structure 816 include, but are not limited to, metals such as stainless steel, polymers, and/or any other suitable material.

In certain embodiments, the lift assembly 810 includes a lifting component 814 mounted on the assembly support structure 816 and movable relative to assembly support structure 816. The lifting component 814 may be vertically movable relative to the assembly support structure 816 and/or a resting position of the lifting component 814. For example, the lifting component 814 may be configured to be lowered and raised into and/or out of vessel 811. In other embodiments, the lift assembly 810 is configured to move the lifting component 814 horizontally or at another angle (for example, 30 degrees (30°), 45°, 60°, etc.) relative to the assembly support structure 816 and/or a resting position of the lifting component 814.

In one embodiment, the vessel 811 comprises an entry port 832 positioned at a bottom portion of the vessel 811, and a lift assembly 810 attached to a top portion of the vessel, the lift assembly comprising an assembly support structure 816 and a lifting component 814 vertically movable relative to the assembly support structure 816 and extendable to at least the entry port 832.

The lifting component 814 may be specifically configured and arranged to move and/or support a particular article or component of the system, such as, for example, a collapsible bag or an impeller. For example, as described below, a lifting component 814 for moving a collapsible bag may be in the form of one or more rods including hooks 820 that can be used to support a collapsible bag in a collapsed or uncollapsed configuration. In another example, a lifting component 814 for moving a magnetic impeller may include magnets for magnetically attracting the impeller.

In one embodiment, in a collapsible bag configured to be contained and supported within a rigid vessel of a mixing and/or reactor system, the improvement comprises a plurality of rods attached to an upper surface of the collapsible bag configured to be engaged by at least one lifting component 814 of a lift assembly to enable the lift assembly to lift and support at least the upper surface of the collapsible bag.

In one set of embodiments, a system comprises a vessel configured to perform mixing and/or a biological, chemical or pharmaceutical reaction process, and a lift assembly attached to the vessel and constructed and arranged to lift at least a portion of an article contained within the vessel from a bottom portion to a top portion of the vessel.

Another aspect of the invention is drawn to methods. In one embodiment, a method for lifting an article contained within a vessel comprises extending a lifting component 814 from a top portion to a bottom portion of a vessel 811, the vessel 811 having an interior portion configured to contain a volume of fluid, and an entry port 832 positioned at the bottom portion of the vessel 811; directing the lifting component 814 towards the entry port 832 such that at least a part of the lifting component 814 is positioned at or near the entry port 832 of the vessel 811; attaching an article to at least a portion of the lifting component 814; and raising the lifting component 814 and the article towards the top portion of the vessel 811.

In another embodiment of the method of the invention, the at least a part of the lifting component 814 positioned at or near the entry port 832 is directed through the entry port 832 such that the at least a part of the lifting component 814 is positioned exterior to the interior portion of the vessel 811 to facilitate being attached to the article.

In some embodiments, the lift assembly 810 comprises a cable 815 which may have a first end connected, either directly or indirectly, to assembly support structure 816 as well as a second end connected, either directly or indirectly, to lifting component 814. A "cable" as used herein is broader than the ordinary meaning of this term in that it may comprise any suitable material (for example, metals such as stainless steel, polymers, natural fibers, elastomeric materials, etc.) in any suitable configuration (for example, chains, ropes, twine, etc.) capable of supporting the component to be moved. The cable 815 may be supported and wound by a reel or other suitable component. In some embodiments, cable 815 may be detachable from lifting component 814 and/or assembly support structure 816. In one embodiment, a lift assembly comprises a cable or chain including a first end connected directly or indirectly to the lifting component and a second end connected directly or indirectly to a motive device, which may be, for example, a motor or a pulley system. A method according to an embodiment of the invention comprises extending the lifting component from the top portion to the bottom portion of the vessel by extending a cable or chain attached to the lifting component.

Assembly support structure 816 may have any suitable configuration that provides adequate mechanical strength to support the lift assembly 810 relative to the vessel and to support the component to be moved (as well as any additional elements attached thereto). In some cases, the assembly support structure 816 may comprise one or more support bars 817, which may be optionally arranged to form a scaffold. In some embodiments, assembly support structure 816 may comprise a plate (not shown) connected to (either directly or indirectly) support structure 812. In yet other embodiments, an assembly support structure 816 comprises a ring having a circumference substantially similar as the circumference of a vessel to which the assembly support structure 816 is attached. An assembly support structure 816 may have any suitable shape and, in some embodiments, may be curved, dome shaped, cylindrical, tubular, or substantially planar. The assembly support structure 816 may comprise any suitable material including, but not limited to, metals (for example, stainless steel), polymers, and so forth.

Lifting component 814 may comprise a variety of elements disposed in a variety of configurations. For example, in some embodiments, the lifting component 814 comprises one or more lifting bars 818 which may, in some embodiments, comprise at least one hook 820 configured to engage a portion of the top of a collapsible bag. Hooks 820 may be used to secure the lifting component 814 to the supported component (for example, a collapsible bag). In other embodiments, the lifting component 814 comprises a single hook 820 and does not include lifting bars 818. In some examples, the lifting component 814 may comprise multiple hooks 820 connected to cable 815 via secondary cables. The lifting bars may be configured to support the collapsible bag in an uncollapsed configuration.

Figure 2:
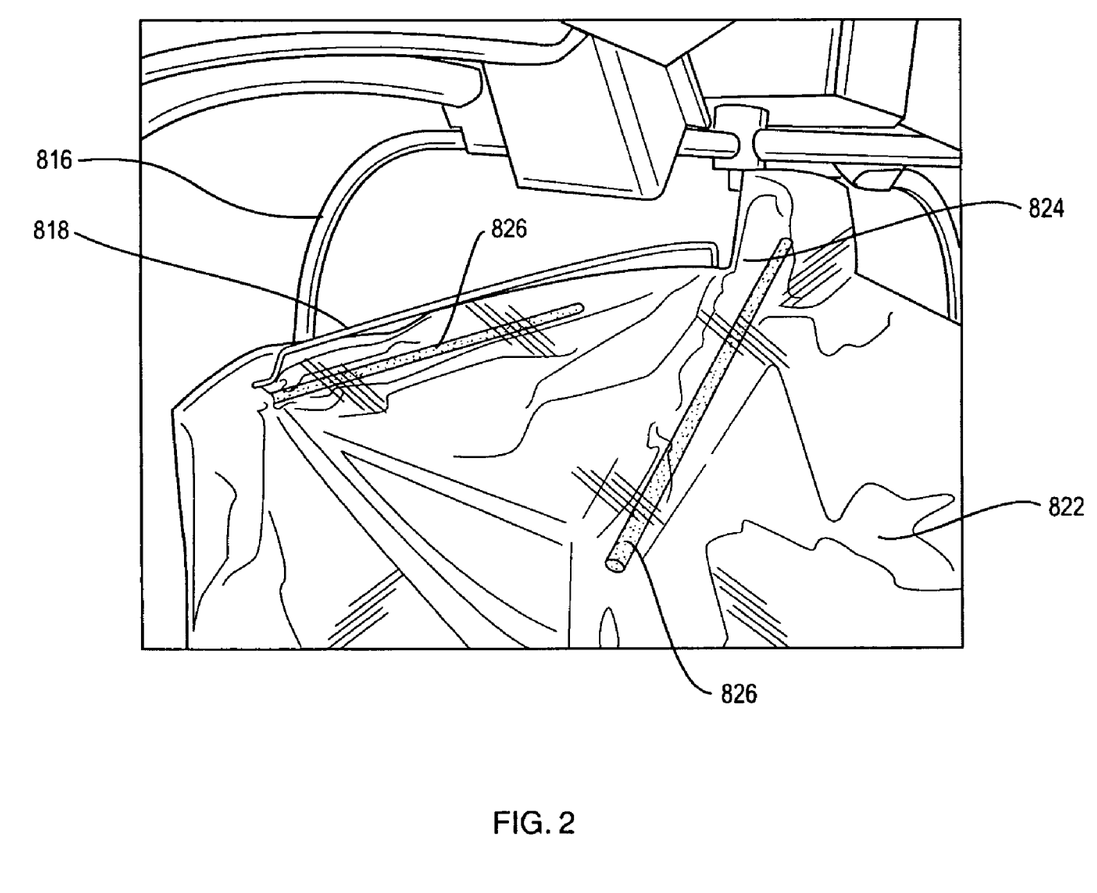
FIG. 2 depicts a top portion of a collapsible bag supported by a lift assembly according to one embodiment of the invention.

In one embodiment, a lift assembly 810 is used to manipulate a collapsible bag and to position the collapsible bag relative to a vessel. FIG. 2 illustrates an exemplary collapsible bag 822 supported by lifting bars 818. In this embodiment, the collapsible bag includes external sleeves 824 which contain reinforcing rods 826. In some cases, the external sleeves are not in fluidic contact with the internal compartment of the collapsible bag. The hooks 820 on the lifting bars 818 may be connected, in some examples, to the collapsible bag via the rods in the external sleeves, as shown in FIG. 2. In some embodiments, the collapsible bag may include one or more eyelets through which the hooks 820 may be connected and the eyelets may be connected to and supported by the reinforcing rods 826. As shown in the embodiment illustrated in FIG. 2, the reinforcing rods 826 may be configured so as to maintain the collapsible bag in an uncollapsed configuration when the upper portion of the bag is supported and positioned at the top of vessel 811 by lift assembly 810. This may facilitate the introduction and/or even distribution of materials in the interior compartment of the collapsible bag.

Referring back to FIG. 1, the lift assembly 810 may also comprise a motive device 828 for moving the lifting component 814 relative to the assembly support structure 816. The lift assembly 810 may comprise any motive device suitable for moving the lifting component 814 including, but not limited to, a motor (as illustrated), a pulley system, and/or a manual crank, among others. In some cases, cable 815 may have a first end operatively associated with or connected, either directly or indirectly, to lifting component 818 as well as a second end operatively associated with or connected, either directly or indirectly, to motive device 828. In some embodiments, cable 815 may be detachable from motive device 828. Motive device 828 may be used to extend or retract the cable, for example, resulting in raising or lowering the lifting component 818. Optionally, an operating panel 830 may be included, for example, on the side of the support structure 812, to control the raising, lowering, and/or stopping of the lifting component 818.

In some embodiments, motive device 828 comprises a motor. The motor (or any other suitable motive device) may be mounted above vessel 811, supported at least in part by assembly support structure 816. The motor and assembly support structure 816 may be oriented in any configuration and manner that provides adequate mechanical strength to support the motor.

Containment structure 812 of vessel 811, may also include, in some cases, an entry port 832 that allows access into the interior of the vessel 811. For example, the entry port 832 can be configured and positioned to allow a user to access the interior of the vessel 811. In another example, the entry port 832 may be used to move an article (for example, a collapsible bag) from a region exterior of the vessel to the interior of the vessel and/or from the interior of the vessel to a region exterior of the vessel. In some embodiments, the moving of the article is facilitated or performed by use of the lift assembly 810. The cross-section of the open area of the entry port 832 may be chosen to accommodate articles of varying sizes. For example, the cross-sectional area of the entry port 832 may be, in some embodiments, at least 10 cm$^2$, at least 50 cm$^2$, at least 100 cm$^2$, at least 1000 cm$^2$, at least 5000 cm$^2$, or at least 1 m$^2$ in size. In one particular embodiment, the entry port 832 is sized to allow passage of a collapsible bag having a volume of, for example, at least 1 L, at least 10 L, at least 50 L, at least 100 L, at least 200 L, at least 500 L, or at least 1,000 L between an exterior and an interior of the vessel, when in a collapsed configuration. In another embodiment, the entry port 832 is sized to allow insertion of an impeller through the port. The entry port 832 may be positioned at any suitable location relative to the containment structure 812 (for example, at or near the bottom, side, near the top, etc. of the containment structure). In an embodiment wherein the entry port 832 is located at or near the top of the containment structure, the lift assembly may be used to lower an article into the vessel.

Figure 3:
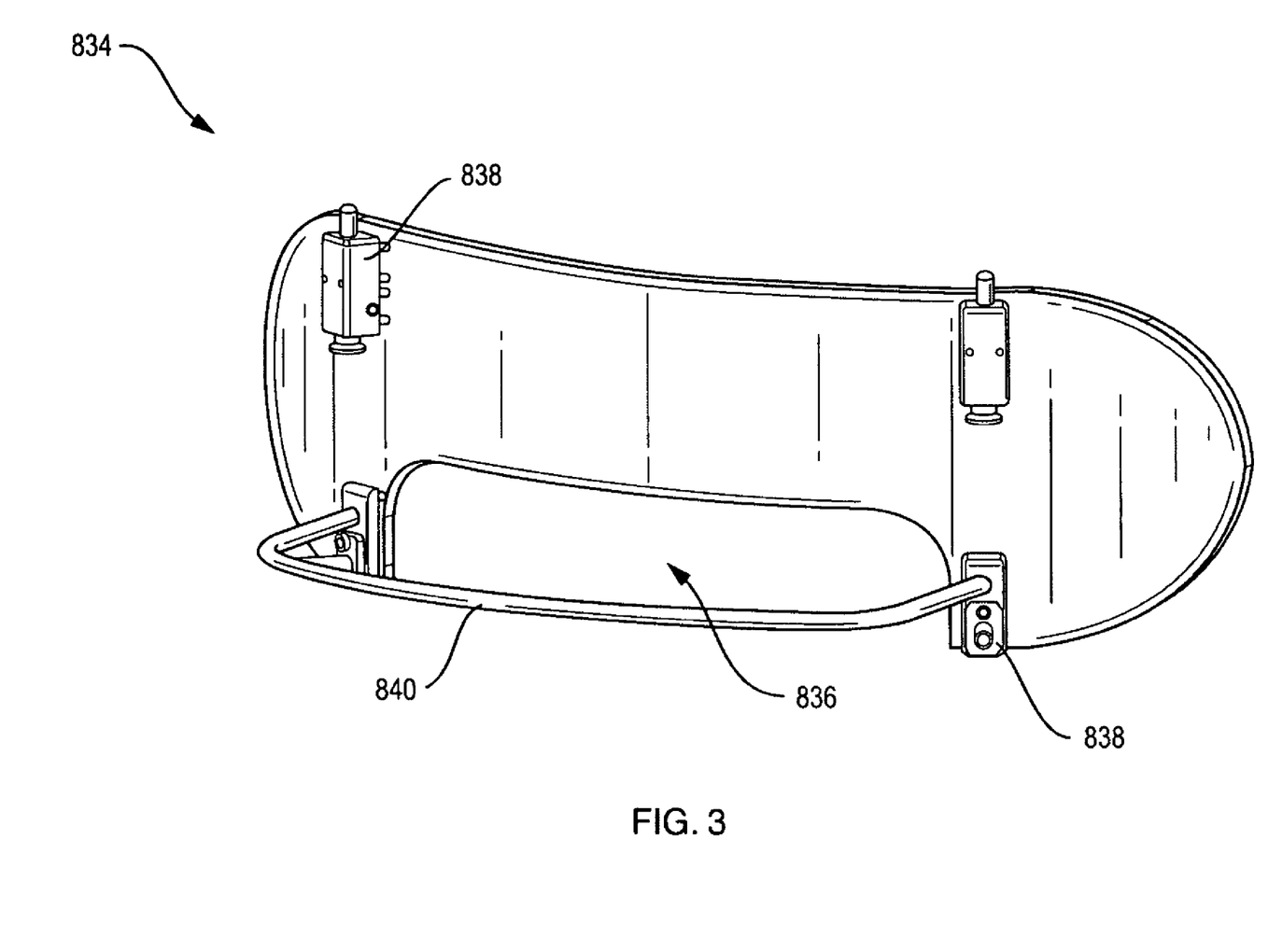
FIG. 3 is a schematic representation of an exemplary entry port cover according to one embodiment of the invention.

In some embodiments, an entry port cover 834 may be used to seal and/or cover at least a portion of the entry port 832. FIG. 3 is a schematic diagram of an exemplary entry port cover 834. Entry port cover 834 may be fabricated from a variety of materials, including for example, metals, polymers, and/or glass, among others. In some embodiments, the entry port cover is at least partially transparent to visible light to allow visual access into the vessel. The entry port cover 834 may be, in some embodiments, removed while an article (for example a collapsible bag) is loaded and/or unloaded, and installed through the entry port. The entry port cover 834 may include, in some examples, a void 836. The void 836 may be of any size such as, for example, at least 1% of the size of the entry port 832, at least 10%, at least 25%, at least 50%, at least 75%, or at least 90% of the size of the entry port 832. The void 836 may also be located in any position on the entry port cover 834 (for example, the bottom, the side, or the top of the entry port cover). The void 836 in certain embodiments allows inlet, outlet, and/or sensor supply lines to be directly connected to inlet, outlet, and/or sensor ports on the collapsible bag contained within the vessel during operation.

The entry port cover 834 may include retractable locking pins 838 used to hold the cover in place on the support container. In one embodiment, the locking pins 838 comprise pressure sensitive pins which are configured to not be able to be manually released by an operator when a pressure is applied to a surface of the entry port cover 834 when mounted in place. For example, the fluid contents of a collapsible bag contained within vessel 811 may force a wall of the bag into pressing contact with the entry port cover 834. In such non-limiting example, when a collapsible bag inside the vessel is full, the collapsible bag exerts a pressure on the locking pins 838 which, in turn, locks them into place until the pressure exerted by the collapsible bag is removed (for example, when some or all of the contents inside the collapsible bag have emptied).

Entry port cover 834 may, in some cases, comprise a probe support bar 840. The probe support bar 840 may be used to immobilize, attach, support, etc. inlet, outlet, and/or sensor supply lines that are to be connected to and/or disconnected from inlet, outlet, and/or sensor ports on a collapsible bag within the vessel. The probe support bar 840 may also support the inlet, outlet, and/or sensor supply lines while they are connected to the inlet, outlet, and/or sensor ports on a collapsible bag within the vessel 811. In some cases, supporting the inlet, outlet, and/or sensor supply lines with the probe support bar 840 may prevent tearing of the collapsible bag within the vessel.

Figure 4:
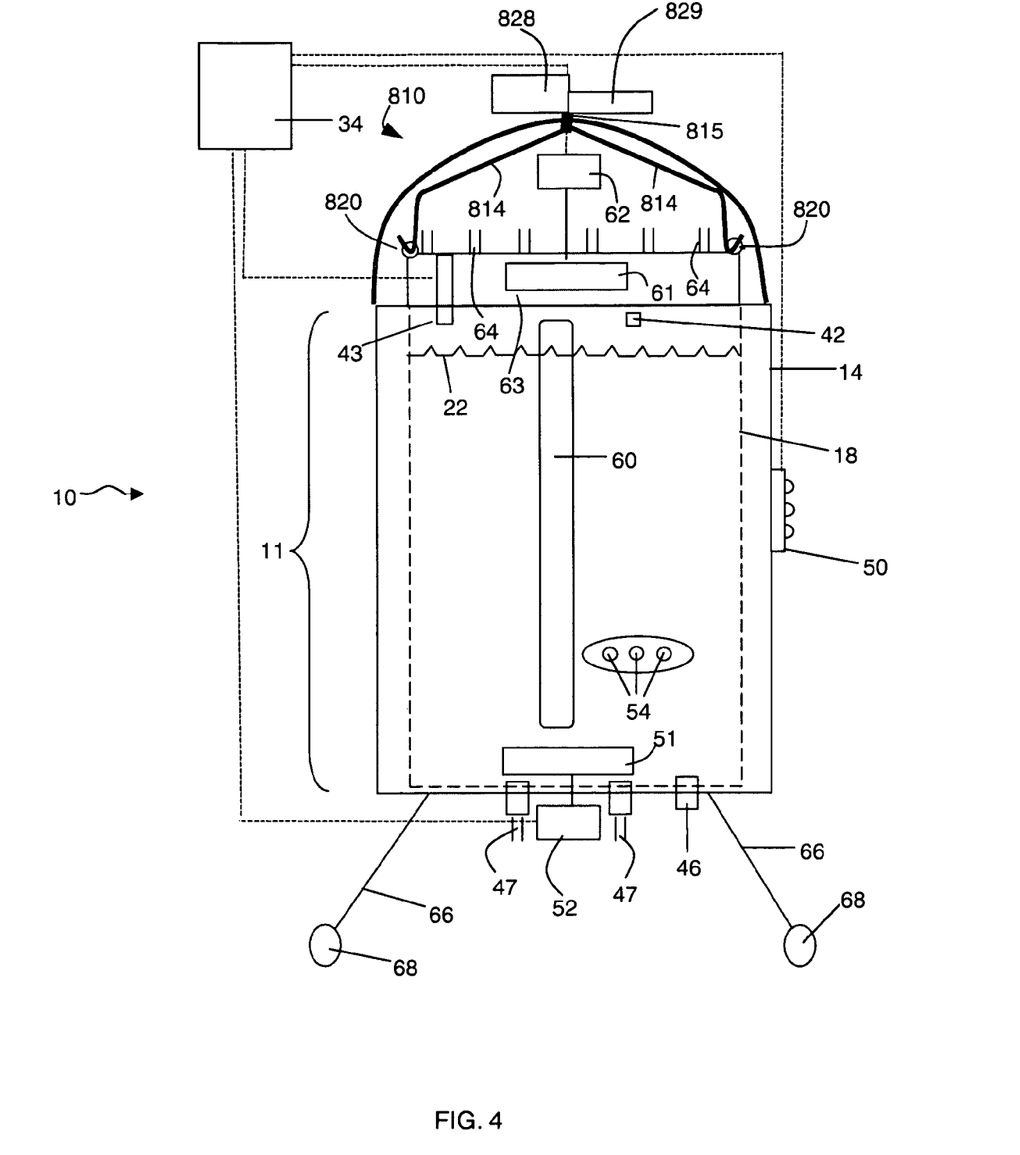
FIG. 4 is a schematic representation of a container contained within a support structure according to one embodiment of the invention.

The following describes an exemplary method of positioning, supporting, moving and/or installing a component with respect to a vessel using a lift assembly 810 of certain embodiments of the invention. While the example below describes the use of a collapsible bag, lifting bars, hooks, and a motor, any of these components may be omitted or replaced with acceptable substitutes (for example, an impeller in the case of the collapsible bag, a pulley system in the case of the motor, etc.) in other embodiments. In one embodiment, a collapsible bag 822, as shown in FIG. 2, is positioned in front of the entry port 832 (for example, as shown in FIG. 1) exterior to the vessel). The operator moves or removes the entry port cover 834 (for example, as shown in FIG. 3) to allow access into the vessel 811 (as shown in FIG. 1; vessel 11 as shown in FIG. 4). FIG. 2 shows the lifting bars 818 of the lift assembly 810. The lifting bars 818 are lowered as the cable 815 (shown in FIG. 1) is extended from a reel 829 operatively associated with the motive device or motor 828.

The lifting bars 818 can be lowed until they are at least positioned at the level of the entry port 832. Once the lifting bars 818 are positioned so that they are either at or near the entry port, or in some cases, able to be pulled through the entry port 832 (for example, by a user) such that all or a portion of the lifting bars 818 are exterior to the vessel 811, the motor 828 is stopped. The lifting bars 818 can then be secured to the collapsible bag 822 (as shown in FIG. 2), for example, to reinforcing rods 826 (shown in FIG. 2). In some embodiments, the lifting bars 818 may be removed from the cable 815 (FIG. 1) prior to attaching the collapsible bag 822 to the lifting bars 818. In a case in which the lifting bars 818 are detached from the cable 815 prior to securing the collapsible bag 822, the lifting bars 818 may be reattached to the cable 815 prior to lifting. Once the collapsible bag 822 is attached, the lifting bars 818 are raised as the cable 815 is retracted by the motor 828. This lifting motion pulls the collapsible bag 822 upward, and/or into the interior of the vessel 811 and upward. At least the upper portion of the collapsible bag 822 can then be lifted into position (see FIG. 2) by the lifting bars 818, thereby expanding the collapsible bag 822 along its length and/or width, for example, from a collapsed to an uncollapsed configuration.

Once the collapsible bag 822 is expanded and positioned, the operator may replace the entry port cover 834, ensuring that the locking pins 838 are engaged. Once the collapsible bag 822 has been positioned and the entry port cover 834 has been secured, the system 800 is ready for operation and, for example, the collapsible bag 822 may be filled with liquid. In some embodiments, operation (for example, performance of a chemical reaction) of the vessel 811 takes place while the collapsible bag 822 remains attached to the lift assembly 810 (as illustrated in FIG. 2). Alternatively, the lift assembly 810 may be removed from the collapsible bag 822 prior to or during operation of the vessel 811.

Once operation of the vessel 811 has been completed, it may be desirable to remove the collapsible bag 822 from the vessel 811, for example, to allow positioning of a replacement collapsible bag 822 inside the vessel 811 to allow a second operation to be performed. To remove the collapsible bag 822 from the vessel 811, for example, after contents from the interior of the collapsible bag 822 have been emptied, the entry port cover 834 of the vessel 811 can be removed. The lifting bars 818 can be lowered, the collapsible bag 822 can be pulled through the entry port 832 to the exterior of the vessel 811, and the collapsible bag 822 may be disconnected from the hooks 820 on the lifting bars 818. Once the collapsible bag 822 is disconnected, a new bag may optionally be attached to the lifting bars 818, and the lifting bars 818 may be raised towards the top of the lift assembly 810 using the motor 828, and the entry port cover 834 may again be secured over the bag entry port 832.

The lift assembly 810 may also include a variety of safety features in certain embodiments. For example, the lift assembly 810 may be designed to control the speed with which various parts of the lifting assembly 810 are moved (for example, raised and lowered). Strain interlocks may be incorporated, in some embodiments, to prevent or reduce damage to the component being lifted in the event, for example, of a snag. For example, strain interlocks may be used to prevent the tearing of a collapsible bag 822 that may be caught or obstructed during installation or removal. In addition, a "Stop" button may be included on the operating panel and/or controller to allow the operator to manually intervene during installation or removal of the lifted component.

In some embodiments, more than one lift assembly 810 may be integrated into a system described herein. For example, in some cases, separate lifts may be used to move multiple components (for example, filters, tubing, assemblies, powder bags, liquid bags, etc.) in a single vessel 811.

A wide variety of vessel types can potentially be configured with the lift assemblies 810 described herein. In some embodiments, the vessel 811 is configured to contain a volume of liquid. For example, FIG. 4 is a schematic representation of one embodiment of a bioreactor system 10*a* including a container 18, such as a flexible container, and a lift assembly 810 configured to lift and support the flexible container 18 is shown in FIG. 4. As shown in the embodiment illustrated in FIG. 4, system 10, includes a vessel 11, which can in certain embodiments be substantially similar in design and configuration as vessel 811 shown previously by the embodiment shown in FIG. 1, and includes a reusable support structure 14, which in one embodiment is a stainless steel tank that surrounds and contains a container 18.

In some embodiments, the container 18 is configured as a collapsible bag, for example, a polymeric bag. Additionally or alternatively, all or portions of the collapsible bag or other container 18 may comprise a substantially rigid material such as a rigid polymer, metal, and/or glass. In other embodiments, a rigid container is used in this configuration. The container 18 may be single use or disposable and may be configured to be easily removable from the support structure 14. In some embodiments, the container 18 is non-integrally connected to the support structure 14.

If a collapsible bag is used as the container 18, the collapsible bag may be constructed and arranged for containing a liquid 22, which may contain reactants, media, and/or other components necessary for carrying out a desired process such as a chemical or biological reaction. The collapsible bag may also be configured such that liquid 22 remains substantially in contact only with the collapsible bag during use and not in contact with support structure 14. In such embodiments, the collapsible bag may be disposable and used for a single reaction or a single series of reactions, after which the bag is discarded. If the liquid in the collapsible bag does not come into contact with the support structure 14, the support structure 14 can be reused without cleaning. That is, after a reaction takes place in container 18, the container 18 can be removed from the support structure 14 and replaced by a second container, which may be disposable. A second reaction can be carried out in the second container without having to clean either the first container 18 or the reusable support structure 14.

Also shown in the embodiment depicted in FIG. 4 are an optional inlet port 42 (located near the top of the container 18), and an optional outlet port 46 (located near the bottom of the container 18), which can be formed in the container 18 and/or reusable support structure 14 and can facilitate more convenient introduction and removal of a liquid and/or gas from the container 18. The container 18 may have any suitable number of inlet ports and any suitable number of outlet ports. A plurality of inlet ports may be used to provide different gas compositions for example, via a plurality of spargers 47, and/or to allow separation of gases prior to their introduction into the container 18. These ports may be positioned in any suitable location with respect to container 18. For example, for certain vessels including spargers 47, the container may include one more gas inlet ports 47 located at a bottom portion of the container 18. Tubing may be connected to the inlet and/or outlet ports to form, for example, delivery and harvest lines, respectively, for introducing and removing liquid from the container 18. Optionally, the container 18 or the support structure 14 may include a utility tower 50, which may be provided to facilitate interconnection of one or more devices internal to the container 18 or to the support structure 14 with one or more pumps, controllers, and/or electronics (for example, sensor electronics, electronic interfaces, and pressurized gas controllers) or other devices. Such devices may be controlled using a control system 34.

For systems including multiple spargers 47, control system 34 may be operatively associated with each of the spargers 47 and configured to operate the spargers 47 independently of each other. This can allow, for example, control of multiple gases being introduced into the container 18.

In general, as used herein, a component of an inventive system that is "operatively associated with" one or more other components indicates that such components are directly connected to each other, in direct physical contact with each other without being connected or attached to each other, or are not directly connected to each other or in contact with each other, but are mechanically, electrically (including via electromagnetic signals transmitted through space), or fluidically interconnected so as to cause or enable the components so associated to perform their intended functionality.

As shown in the embodiment illustrated in FIG. 4, the vessel 11 may optionally include a mixing system such as an impeller 51, which can be rotated, for example, about a single axis, using an impeller motor 52 that can be external to the container 18. In some embodiments, as described in more detail below, the impeller 51 and impeller motor 52 are magnetically coupled. The mixing system can be controlled by control system 34.

Additionally or alternatively, the vessel 11 may include an antifoaming system such as a mechanical antifoaming device. As shown in FIG. 4, an antifoaming device may include in the headspace of the container 18, for example, a second impeller 61 that can be rotated (for example, magnetically) using a second motor 62, which may be external to the container 18. The second impeller 61 can be used to collapse a foam contained in a head space 63 of the container 18 or used to concentrate cells and return them to the culture fluid below via centrifugal force. In some embodiments, the antifoaming system is in electrical communication with a sensor 43 (for example, a foam sensor) via control system 34. The sensor 43 may determine, for example, the level or amount of foam in the head space 63 or the pressure in the container 18, which can trigger regulation or control of the antifoaming system. In other embodiments, the antifoaming system is operated independently of any sensors.

The support structure 14 and/or the container 18 may also include, in some embodiments, one or more ports 54 that can be used for sampling, analyzing (for example, determining pH and/or amount of dissolved gases in the liquid), or for other purposes. The support structure 14 may also include one or more site windows 60 for viewing a level of liquid 22 within the container 18. One or more connections 64 may be positioned at a top portion of the container 18 or at any other suitable location. Connections 64 may include openings, tubes, and/or valves for adding or withdrawing liquids, gases, and the like from the container 18, each of which may optionally include a flow sensor and/or filter (not shown). The support structure 14 may further include a plurality of legs 66, optionally with wheels 68 for facilitating transport of the vessel 11.

It should be understood that not all of the features shown in FIG. 4 need be present in all embodiments of the invention and that the illustrated elements may be otherwise positioned or configured. Also, additional elements may be present in other embodiments, such as the elements described herein.

Various aspects of the present invention are directed to a vessel including a container such as a collapsible bag, semi-rigid or rigid vessel. "Flexible container", "flexible bag", or "collapsible bag" as used herein, indicates that the container or bag is unable to maintain its shape and/or structural integrity when subjected to the internal pressures expected during operation. Such pressure (for example, due to the weight and/or hydrostatic pressure of liquids and/or gases contained therein) without the benefit of a separate support structure. The collapsible bag 822 (in FIG. 2) may be made out of inherently flexible materials, such as many plastics, or may be made out of what are normally considered rigid materials (for example, glass or certain metals) but having a thickness and/or physical properties rendering the container as a whole unable to maintain its shape and/or structural integrity when subjected to the internal pressures expected during operation without the benefit of a separate support structure. In some embodiments, collapsible bags include a combination of flexible and rigid materials; for example, the bag may include rigid components such as connections, ports, supports for a mixing and/or antifoaming system, etc.

The container 18 (for example, collapsible bag 822) may have any suitable size for containing a liquid. For example, the container 18 may have a volume from about one liter (1 L) to about 10,000 liters (10,000 L), or from about 40 liters (40 L) to about 5,000 liters (5,000 L), or from about 100 L to about 2000 L, or from about 200 L to about 1,000 L, or from about 500 L to about 750 L. Volumes greater than 10,000 L are also possible. An exemplary embodiment of the invention is a bioreactor that comprises a 1,000 liter bag.

In some embodiments, the collapsible bag 822 is disposable and is formed of a suitable flexible material or combination of rigid and flexible. The flexible material may be one that is USP Class VI certified, for example, silicone, polycarbonate, polyethylene, and polypropylene. Non-limiting examples of flexible materials include polymers such as polyethylene (for example, linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. As noted above, portions of the flexible container or collapsible bag 822 may comprise a substantially rigid material such as a rigid polymer (for example, high density polyethylene), metal, and/or glass (for example, in areas for supporting fittings). In other embodiments, the container 18 comprises substantially rigid material.

All or portions of the container 18 may be optically transparent to allow viewing of contents inside the container. For example, FIG. 4 depicts site window 60. The materials or combination of materials used to form the container 18 may be chosen based on one or more properties such as flexibility, puncture strength, tensile strength, liquid and gas permeabilities, opacity, and adaptability to certain processes such as blow molding, injection molding, or spin cast molding (for example, for forming seamless collapsible bags).

The container, such as, for example, a collapsible bag, may have any suitable thickness for holding a liquid and may be designed to have a certain resistance to puncturing during operation or while being handled. For example, the walls of a container may have a total thickness of less than or equal to 250 mils or 6,350 micrometers ($\mu m$). One mil is equal to 25.4 micrometers (25.4 $\mu m$). The walls of a container suitable for use in other embodiments may be from about 10 mils to about 250 mils (from about 254 $\mu m$ to about 6,354 $\mu m$), or from about 15 mils to about 200 mils (from about 381 $\mu m$ to about 5,080 $\mu m$), or from about 25 mils to about 100 mils (from about 635 $\mu m$ to about 2,540 $\mu m$), or from about 50 mils to about 70 mils (from about 1,270 $\mu m$ to about 1,778 $\mu m$).

In some embodiments, the container 18 includes more than one layer of material that may be laminated together or otherwise attached to one another to impart certain properties to the container 18. For example, one layer may be formed of a material that is substantially oxygen impermeable. Another layer may be formed of a material to impart tensile strength or resistance to breaking or tearing to the container 18. Yet another layer may be included to impart chemical resistance to fluid that may be contained in the container 18. It should be understood that a container may be formed of any suitable combinations of layers and that the invention is not limited in this respect. The container 18, for example, a collapsible bag 822 as shown in FIG. 2, may include, from 1 layer to about 6 layers of material, or from about 2 layers to about 5 layers of material, or from about 3 layers to about 4 layers of material, wherein the material of each layer is the same or different.

Each layer may have a thickness of, for example, from about 3 mils to about 200 mils (76.2 $\mu m$ to about 5,080 $\mu m$), or from about 5 mils to about 100 mils (127 $\mu m$ to about 2,540 $\mu m$), or from about 10 mils to about 50 mils (254 $\mu m$ to about 1,270 $\mu m$), or from about 15 mils to about 25 mils (381 $\mu m$ to about 635 $\mu m$), or combinations thereof.

In some embodiments of the invention, the container 18 is seamless. The container may be, for example, a seamless collapsible bag, a seamless rigid container, or a seamless semi-rigid container. Seamless containers are described in more detail in U.S. patent application Ser. No. 11/818,901 filed on Jun. 15, 2007 and entitled, "Gas Delivery Configurations, Foam Control Systems, and Bag Molding Methods and Articles for Collapsible Bag Vessels" by Fisher et al., the teachings of which are incorporated herein by reference in their entireties.

In some embodiments, components that are integrated with collapsible bags or other containers using methods described herein are formed in one or more materials that are USP Class VI certified. Examples of such include silicone, polycarbonate, polyethylene, and polypropylene. Non-limiting examples of materials that can be used to form components include polymers such as polyethylene (for example, low density polyethylene and high density polyethylene), polypropylene, polyvinylchloride, polyvinyldichloride, polyvinylidene chloride, ethylene vinyl acetate, polyvinyl alcohol, polycarbonate, polymethacrylate, nylon, silicone rubber, other synthetic rubbers and/or plastics, and combinations thereof. Ceramics, metals, and magnetic materials can also be used to form all or portions of a component. In some embodiments, all or portions of a component are rigid; in other embodiments, all or portions of a component are flexible. A material used to form a component may be chosen based on, for example, the function of the component and/or one or more properties such as compatibility with the container, flexibility, tensile strength, hardness, liquid and gas permeabilities, and adaptability to certain processes such as blow molding, injection molding, or spin cast molding.

In certain embodiments, especially in certain embodiments involving fluid manipulations or carrying out a chemical or biological reaction in a container such as a collapsible bag 822, the container is substantially closed. For example, the container is substantially sealed from the environment outside of the container except, in certain embodiments having one or more inlet and/or outlet ports 54, as shown in FIG. 4. The outlet ports 54 allow addition to, and/or withdrawal of contents from, the container 18. If a collapsible bag 822 is used, it may be substantially deflated prior to being filled with a liquid, and may begin to inflate as it is filled with liquid. In other embodiments, aspects of the invention can be applied to opened container systems.

In some cases, fluids may be introduced and/or removed from a vessel via one or more inlet ports and/or outlet ports in the container 18. The vessel 11 may be a part of a reactor system for performing a biological or chemical reaction. In some cases, pumps, such as disposable pumps, may be used to introduce a gas or other fluid into the container, for example, via an inlet port, and/or which may be used to remove a gas or other fluid from the container, for example, via an outlet port. For example, a magnetically-coupled pump may be created by encasing a disposable magnetic impeller head in an enclosure with inlet(s) and outlet(s) that achieves fluid pumping. Flexible and/or curved blades may be used to enhance pumping or provide pressure relief. In another embodiment, pumping of fluids, gas and/or powder may be achieved without pump heads and/or pump chambers by sequentially squeezing, for example, an electromechanical-polymeric tube that effectively achieves "peristalsis." One way valves in the tube may optionally be used, which may aid in the prevention of backflow. In certain embodiments, the collapsible bag can contain heat conductors embedded in the bag to facilitate heat transfer. In certain embodiments, the collapsible bag can contain heat conductors embedded in the bag to facilitate heat transfer as further described in U.S. patent application Ser. No. 12/011,493 entitled, "Bag Wrinkle Remover, Leak Detection Systems, and Electromagnetic Agitation for Liquid Containment Systems," which is incorporated herein by reference.

As shown in FIG. 4, one embodiment of the present invention may include a support structure 14, which can surround, support, and contain container 18. The support structure 14 may have any suitable shape able to surround and/or contain the container. In some cases, the support structure is reusable. The support structure may be formed of a substantially rigid material. Non-limiting examples of materials that can be used to form the reusable support structure include stainless steel, aluminum, glass, resin-impregnated fiberglass or carbon fiber, polymers (for example, high-density polyethylene, polyacrylate, polycarbonate, polystyrene, nylon or other polyamides, polyesters, phenolic polymers, and combinations thereof. The materials may be certified for use in the environment in which it is used. For example, non-shedding materials may be used in environments where minimal particulate generation is required.

In some embodiments, the reusable support structure may be designed to have a height and diameter similar to standard stainless steel bioreactors (or other standard reactors or vessels). The design may also be scalable down to small volume bench reactor systems. Accordingly, the reusable support structure may have any suitable volume for carrying out a desired chemical, biochemical and/or biological reaction. In many examples, the reusable support structure has a volume substantially similar to that of the container. For example, a single reusable support structure may be used to support and contain and single container having a substantially similar volume. In other cases, however, a reusable support structure is used to contain more than one container. The reusable support structure may have a volume between, for example, of from about 1 liter (1 L) to about 10,000 liters (10,000 L); from about 10 L to about 5,000 L, from about 100 L to about 2,000 L, from about 500 L to about 1000 L. Volumes greater than 10,000 L are also possible.

In other embodiments, however a vessel of the present invention does not include a separate container (for example, collapsible bag) and support structure, but instead comprises a self-supporting disposable container. The container may be, for example, a plastic vessel and, in some cases, may include an agitation system integrally or removably attached thereto. The agitation system may be disposable along with the container. In one particular embodiment, such a system includes an impeller welded or bolted to a polymeric container. It should therefore be understood that many of the aspects and features of the vessels described herein with reference to a container and a support structure (for example, a seamless container, a sparging system, an antifoaming device, etc.), are also applicable to a self-supporting disposable container.

As an example, a container, such as container 18 shown in FIG. 4, may include various sensors and/or probes for controlling and/or monitoring one or more process parameters inside the disposable container such as, for example, temperature, pressure, pH, dissolved oxygen (DO), dissolved carbon dioxide ($DCO_2$), mixing rate, and gas flow rate. The sensor may also be an optical sensor in some cases.

In some embodiments, process control may be achieved in ways which do not compromise the sterile barrier established by a disposable container. For example, gas flow may be monitored and/or controlled by a rotameter or a mass flow meter upstream of an inlet air filter. In another embodiment, disposable optical probes may be designed to use "patches" of material containing an indicator dye which can be mounted on the inner surface of the disposable container and read through the wall of the disposable container 18 via a site window 60 (FIG. 4) in the reusable support structure 14. For example, dissolved oxygen, pH, and/or $CO_2$ each may be monitored and controlled by an optical patch and sensor mounted on, for example, a gamma-irradiatable, biocompatible polymer which, can be sealed to, embedded in, or otherwise attached to the surface of the container 18.

Figure 5:
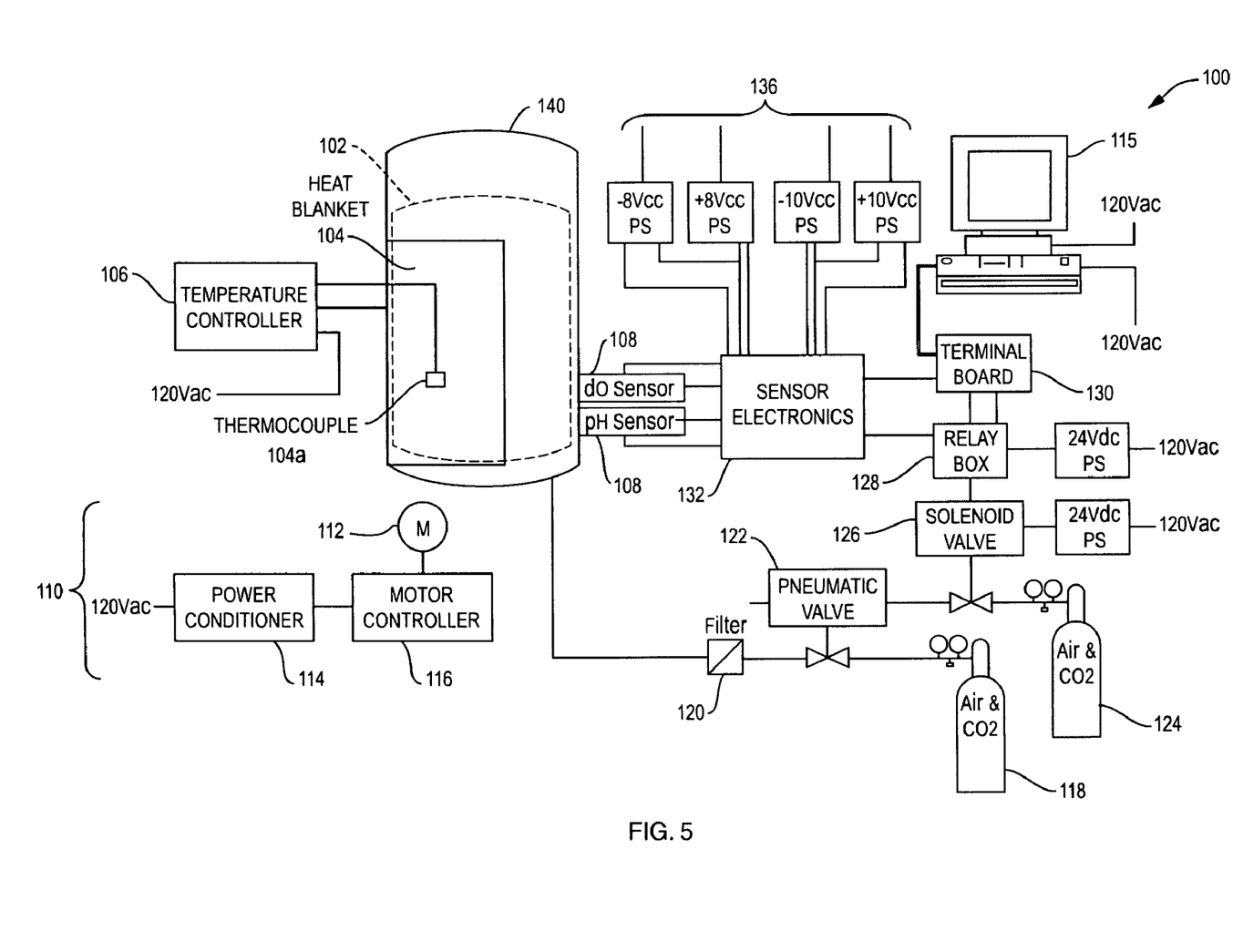
FIG. 5 depicts a system for carrying out fluid manipulations including biological and chemical processes, according to another embodiment of the invention.

For example, turning to FIG. 5, the illustrated embodiment depicts a disposable bioreactor system 100 according to one embodiment of the invention. The reusable support structure or containment structure 140 encloses and supports a collapsible bag or other container 102 which may be operatively associated with a temperature controller 106, non-limiting examples of which are a heat exchanger, a closed loop water jacket, an electric heating blanket 104, and a Peltier heater. A heater may also include a thermocouple 104a and/or a resistance temperature detector (RTD) for sensing a temperature of the contents inside the container 102. The thermocouple 104a may be operatively connected to the temperature controller 106 in order to control temperature of the contents in the container 102. Optionally, a heat-conducting material may be embedded in the surface of the container 102 to provide a heat transfer surface to overcome the insulating effect of the material used to form other portions of the container 102.

Cooling may also be provided by a closed loop water jacket cooling system, a cooling system mounted on the reactor, or by standard heat exchange through a cover/jacket on the reusable support structure (for example, the heat blanket 104). Alternatively, a packaged dual unit which provides heating and cooling may include a component of a device configured for both heating/cooling, but may also be separate from a cooling jacket. Cooling may also be provided by Peltier coolers. For example, a Peltier cooler may be applied to an exhaust line to condense gas in the exhaust air, in order to help prevent an exhaust filter from wetting out.

In certain embodiments, a reactor system includes gas cooling for cooling the head space and/or exit exhaust. For example, jacket cooling, electrothermal and/or chemical cooling, or a heat exchanger may be provided at an exit air line and/or in the head space of the container. This cooling can enhance condensate return to the container, which can reduce plugging and fouling of an exit air filter. In some embodiments, purging of pre-cooled gas into the head space can lower the dew point and/or reduce water vapor burden of the exit air gas.

In some embodiments of the disclosed system, sensors and/or probes (for example, sensors 108) may be connected to a sensor electronics module 132, the output of which can be sent to a terminal board 130 and/or a relay box 128. Sensor electronics module 132 is operably connected to one or more power supply units 136. As the terms are generally used by those of skill in the relevant art, "VCC" is an electronics designation that refers to voltage from a power supply connected to the collector terminal of a bipolar transistor. In an NPN bipolar junction transistor, such is designated +VCC, while in a PNP transistor, it is −VCC. The embodiment depicted in FIG. 5 comprises a combination NPN and PNP transistors.

The results of the sensing operations may be input into a computer-implemented control system 115 (for example, a computer) for calculation and control of various parameters (for example, temperature and weight/volume measurements) and for display and user interface. Such a control system 115 may also include a combination of electronic, mechanical, and/or pneumatic systems to control heat, air, and/or liquid delivered to or withdrawn from the disposable container as required to stabilize or control the environmental parameters of the process operation. It should be appreciated that the control system 115 may perform other functions and the invention is not limited to having any particular function or set of functions.

The one or more control systems can be implemented in numerous ways, such as with dedicated hardware and/or firmware, using a processor that is programmed using microcode or software to perform the functions recited above or any suitable combination of the foregoing. A control system may control one or more operations of a single reactor for a biological, biochemical or chemical reaction, or of multiple (separate or interconnected) reactors.

Each of systems described herein (for example, with reference to FIG. 5), and components thereof, may be implemented using any of a variety of technologies, including software (for example, C, C#, C++, Java, or a combination thereof), hardware (for example, one or more application-specific integrated circuits), firmware (for example, electrically-programmed memory) or any combination thereof.

Various embodiments according to the invention may be implemented on one or more computer systems. These computer systems, may be, for example, general-purpose computers such as, for example, those based on INTEL® processors such as PENTIUM® or XSCALE® (INTEL Corporation, Inc.). It should be appreciated that one or more of any type of computer system may be used to implement various embodiments described herein. The computer system may include specially-programmed, special-purpose hardware, for example, an application-specific integrated circuit (ASIC). Various components may be implemented in software, hardware or firmware, or any combination thereof. Further, such methods, acts, systems, system elements and components thereof may be implemented as part of the computer system described above or as an independent component.

In one embodiment, a control system operatively associated with a vessel described herein is portable. The control system may include, for example, all or many of the necessary controls and functions required to perform a fluidic manipulation (for example, mixing and reactions) in the bioreactor system 100. The control system may include a support and wheels for facilitating transport of the vessel. Advantageously, such a portable control system can be programmed with set instructions, if desired, transported (optionally with the vessel), and hooked up to a vessel, ready to perform a fluid manipulation in a shorter amount of time than the time required for set up of conventional fluid manipulation control systems. For example, the disclosed system can be set up in less than 1 week, or from less than one hour to about 3 days, from about 3 hours to about 12 hours.

A vessel, including the container 102, may also be connected to one or more sources of gases such as air, oxygen, carbon dioxide, nitrogen, ammonia, or mixtures thereof, in various aspects of the invention. The gases are generally compressed, and may be controllably released or pumped. Such gases may be used to provide suitable growth and/or reaction conditions for producing a product inside the container. The gases may also be used to provide sparging to the contents inside the container, for example, for mixing or other purposes. For example, in certain embodiments employing spargers, bubble size and distribution can be controlled by passing an inlet gas stream through a porous surface prior to being added to the container. Additionally, the sparging surface may be used as a cell separation device by alternating pressurization and depressurization (or application of vacuum) on the exterior surface of the porous surface, or by any other suitable method.

As a specific example, FIG. 5 shows various sources of gases 118 and 124. The inlet gases may optionally pass through filter 120 and/or a flow meter and/or valve 122, which may be controlled by controller system 115, prior to entering the container. Valve 122 may be a pneumatic actuator (actuated by, for example, compressed air/carbon dioxide or other gas 124), which may be controlled by a solenoid valve 126. These solenoid valves may be controlled by a relay 128 connected to terminal board 130, which is connected to the controller system 115. The terminal board may comprise, for example, a PCI terminal board, or a USB/parallel, or fire port terminal board of connection. In other embodiments, flush closing valves can be used for addition ports, harvest and sampling valves. Progressive tubing pinch valves that are able to meter flow accurately can also be used. In some cases, the valves may be flush closing valves (for example, for inlet ports, outlet ports, sampling ports, etc.). The inlet gases may be connected to any suitable inlet of the vessel. In one embodiment, the inlet gases are associated with one or more spargers which can be controlled independently, as described in more detail below.

As shown in the exemplary embodiment illustrated in FIG. 5, the container and support structure illustrated in FIG. 4 or FIG. 1 can be operatively associated with a variety of components as part of an overall bioreactor system 100, according to another aspect of the invention. Accordingly, the container and/or support structure may include several fittings to facilitate connection to functional component such as filters, sensors, and mixers, as well as connections to lines for providing reagents such as liquid media, gases, and the like. The container and the fittings may be sterilized prior to use so as to provide a "sterile envelope" protecting the contents inside the container from airborne contaminants outside. In some embodiments, the contents inside the container do not contact the reusable support structure and, therefore, the reusable support structure can be reused after carrying out a particular chemical, biochemical and/or biological reaction without being sterilized, while the container and/or fittings connected to the container can be discarded. In other embodiments, the container, fittings, and/or reusable support structure may be reused (for example, after cleaning and sterilization).

A vessel may also include a mixing system for mixing contents of the container. In some cases, more than one agitator or mixer may be used, and the agitators and/or mixers may the same or different. More than one agitation system may be used, for example, to increase mixing power. In some cases, the agitator may be one in which the height can be adjusted, for example, such that the draft shaft allows raising of an impeller or agitator above the bottom of the tank and/or allows for multiple impellers or agitators to be used. A mixing system of a vessel may be disposable or intended for a single use (for example, along with the container), in some cases.

Various methods for mixing fluids can be implemented in the container. For example, mixers based on magnetic actuation, sparging, and/or air-lift can be used. Direct shaft-drive mixers that are sealed and not magnetically coupled can also be used. In one particular embodiment, mixing systems such as the ones disclosed in U.S. patent application Ser. No. 11/147,124, filed Jun. 6, 2005, entitled "Disposable Bioreactor Systems and Methods," by G. Hodge, et al., published as U.S. Patent Application Publication No. 2005/0272146 on Dec. 8, 2005, that is incorporated herein by reference in its entirety, are used with embodiments described herein.

For example, the mixing system may include a motor 112, for example, for driving an impeller (or other component used for mixing) positioned inside the container, a power conditioner 114, and/or a motor controller 116.

The mixing system may comprise, for example, a magnetic agitator. Typically, a magnetic agitator uses magnets such as fixed or permanent magnets to rotate or otherwise move the agitator, for example, impellers, blades, vanes, plates, cones, etc. In some cases, the magnets within the magnetic agitator are stationary and can be turned on or activated in sequence to accelerate or decelerate the agitator, for example, via an inner magnetic impeller hub. As there is no penetration of the container by a shaft, there may be no need to maintain the agitator in a sterile condition, for example, using internal and/or external rotating seals, live hot steam, or the like.

Specific non-limiting examples of devices that can be used as a mixing system, and/or an antifoaming system in certain embodiments, are described in U.S. patent application Ser. No. 11/818,901, filed on Jun. 15, 2007 and entitled, "Gas Delivery Configurations, Foam Control Systems, and Bag Molding Methods and Articles for Collapsible Bag Vessels" by Fisher et al., which is incorporated herein by reference in its entirety. Such devices may include a magnetically-actuated impeller, although other arrangements are possible. In some configurations, the impeller is magnetically actuated and the motor is not directly connected to the impeller. Magnets associated with a drive head can be aligned with magnets associated with an impeller hub, such that the drive head can rotate the impeller through magnetic interactions. In some cases, the motor portion (and other motor associated components) may be mounted on a support structure.

The impeller systems described herein may allow the system to mix fluids, solids, or foams of any type. For example, fluids inside the container may be mixed to provide distribution of nutrients and dissolved gases for cell growth applications. The same disposable container may be used for mixing buffers and media or other solutions in which a disposable product contact surface is desirable. This may also include applications in which the vessel is not required to be sterile or maintain sterility. Moreover, embodiments described herein enable the container holding the fluid/mixtures/gases to be removed and discarded from the reusable support structure such that the reusable support structure is not soiled by the fluids that are mixed in the container. Thus, the reusable support structure need not to be cleaned or sterilized after every use.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A lift assembly for installing, lifting, or supporting a collapsible bag within a vessel configured to contain a volume of fluid, comprising:

an assembly support structure adapted to be attached at least to opposite sides of a top portion of the vessel wherein the vessel comprises an entry port positioned at a bottom portion of the vessel, the entry port adapted to allow entry of the collapsible bag into the vessel;

a lifting component mounted on the assembly support structure and vertically movable relative to the assembly support structure, and wherein the lifting component is extendable to at least the level of the entry port, the lifting component configured and arranged to be attached to the collapsible bag to be installed in the vessel, or supported or lifted within the vessel, and to lift at least an upper portion of the collapsible bag to convert the collapsible bag from a collapsed to an uncollapsed configuration and to support the collapsible bag in the uncollapsed configuration; and a motive device for vertically moving the lifting component relative to the assembly support structure, wherein the motive device further comprises a motor mounted above the vessel supported at least in part by the assembly support structure and mechanically linked to the lifting component a controller to control the raising, lowering, and/or stopping of the lifting component via the motor, and a strain interlock to prevent tearing of the collapsible bag that may be caught or obstructed during installation or removal.

2. A lift assembly as in claim 1, wherein the lifting component comprises a lifting bar.

3. A lift assembly as in claim 2, wherein the lifting bar comprises a hook configured to engage a portion of the top of the collapsible bag.

4. A lift assembly as in claim 1, wherein the lifting component comprises a plurality of lifting bars.

5. A lift assembly as in claim 1, further comprising a cable or chain including a first end connected directly or indirectly to the lifting component and a second end connected directly or indirectly to the motive device.

6. A lift assembly as in claim 1, wherein the motive device comprises a pulley system.

7. A lift assembly as in claim 1, wherein the assembly support structure comprises one or more support bars, each bar attached at least to opposite sides of a top portion of the vessel.

8. A method for installing and/or lifting a collapsible bag within a vessel with a lift assembly according to claim 1, comprising:

extending the lifting component from a top portion to a bottom portion of the vessel;

directing the lifting component towards the entry port positioned at the bottom portion of the vessel such that at least a part of the lifting component is positioned at or near the entry port;

attaching the collapsible bag to at least a portion of the lifting component;

activating a motor associated with the lifting assembly via a controller to direct the lifting component and the collapsible bag towards the top portion of the vessel;

monitoring strain during lifting and stopping the lifting component if necessary to prevent tearing of the collapsible bag that may be caught or obstructed during installation or removal.

9. A method as in claim 8, wherein extending the lifting component from the top portion to the bottom portion of the vessel comprises extending a cable or chain attached to the lifting component.

10. A method as claimed in claim 8, wherein the at least a part of the lifting component positioned at or near the entry port is directed through the entry port such that the at least a part of the lifting component is positioned exterior to the interior portion of the vessel prior to attaching the article to at least a portion of the lifting component.

11. A lift assembly as in claim 1, wherein the assembly support structure comprises a ring having a circumference substantially similar to the circumference of the vessel to which the assembly support structure is attached.

12. A lift assembly as in claim 1, wherein the assembly support structure has a form that is chosen from a dome shaped structure and a substantially planar structure.

13. A system comprising a vessel comprising: an entry port positioned at a bottom portion of the vessel, the entry port adapted to allow entry of a collapsible bag into the vessel; the collapsible bag configured to contain a volume of a fluid, a support structure surrounding and containing the collapsible bag; and a lift assembly comprising an assembly support structure attached at least to opposite sides of a top portion of the vessel, a lifting component mounted on the assembly support structure and vertically movable relative to the assembly support structure, and wherein the lifting component is extendable to at least the level of the entry port and through the entry port, such that at least a part of the lifting component can be positioned exterior to the interior portion of the vessel to facilitate being attached to an article, the lifting component configured and arranged to be attached to the collapsible bag to be installed in the vessel, or supported or lifted within the vessel, and to lift at least an upper portion of the collapsible bag to convert the collapsible bag from a collapsed to an uncollapsed configuration and to support the collapsible bag in the uncollapsed configuration; and a motive device for vertically moving the lifting component relative to the assembly support structure, wherein the motive device further comprises a motor mounted above the vessel supported at least in part by the assembly support structure and mechanically linked to the lifting component a controller to control the raising, lowering, and/or stopping of the lifting component via the motor, and a strain interlock to prevent tearing of the collapsible bag that may be caught or obstructed during installation or removal.

14. A system as in claim 13, wherein the lifting component comprises at least one lifting bar.

15. A system as in claim 13, wherein the entry port is sized to allow passage of a collapsible bag having a volume of at least 10 L, and wherein the vessel comprises an entry port cover removably attached to the vessel.

16. A system as in claim 13, comprising a plurality of rods attached to an upper surface of the collapsible bag, the rods configured to be engaged by the lifting component of the lift assembly to enable the lift assembly to lift and support at least the upper surface of the collapsible bag.

17. A system as in claim 16, wherein the upper surface of the collapsible bag comprises a plurality of sleeves, and wherein each sleeve contains one of the plurality of rods.

* * * * *